United States Patent
Kovacs

(10) Patent No.: US 11,458,184 B2
(45) Date of Patent: Oct. 4, 2022

(54) COMPOSITIONS AND METHODS FOR TREATING SKIN CONDITIONS, ACNE FORM LESIONS, AND ACNE

(71) Applicant: LAPKO INC., Las Vegas, NV (US)

(72) Inventor: Bruce Kovacs, Irvine, CA (US)

(73) Assignee: LAPKO INC, Las Vegas, NV (US)

( * ) Notice: Subject to any disclaimer, the term of this patent is extended or adjusted under 35 U.S.C. 154(b) by 0 days.

(21) Appl. No.: 17/369,854

(22) Filed: Jul. 7, 2021

(65) Prior Publication Data

US 2022/0008497 A1    Jan. 13, 2022

Related U.S. Application Data

(60) Provisional application No. 63/048,993, filed on Jul. 7, 2020.

(51) Int. Cl.
| | |
|---|---|
| *A61K 36/752* | (2006.01) |
| *A61K 36/38* | (2006.01) |
| *A61K 31/525* | (2006.01) |
| *A61K 47/40* | (2006.01) |
| *A61P 17/10* | (2006.01) |
| *A61K 47/02* | (2006.01) |
| *A61K 9/00* | (2006.01) |
| *A61K 45/06* | (2006.01) |

(52) U.S. Cl.
CPC .......... *A61K 36/752* (2013.01); *A61K 9/0014* (2013.01); *A61K 31/525* (2013.01); *A61K 36/38* (2013.01); *A61K 45/06* (2013.01); *A61K 47/02* (2013.01); *A61K 47/40* (2013.01); *A61P 17/10* (2018.01)

(58) Field of Classification Search
CPC .... A61K 36/38; A61K 36/752; A61K 31/525; A61K 47/40; A61K 33/32; A61K 31/765; A61K 31/728; A61K 31/78
See application file for complete search history.

(56) References Cited

U.S. PATENT DOCUMENTS

| | | | | |
|---|---|---|---|---|
| 2016/0376263 A1* | 12/2016 | Patron | ................ | C07D 413/14 |
| | | | | 514/784 |
| 2017/0087199 A1* | 3/2017 | Patron | ................ | A61K 36/67 |
| 2017/0096418 A1* | 4/2017 | Patron | ................ | A23L 2/52 |

OTHER PUBLICATIONS

Connolly et al., "Acne Scarring—pathogenesis, evaluation, and treatment options", Journal of Clinical Aesthetic Dermatology, 2017, 10(9):12-23.
Halvorsen et al., "Suicidal Ideation, Mental Health Problems, and Social Impairment Are Increased in Adolescents with Acne: A Population-Based Study", The Society for Investigative Dermatology, 2011,131:363-370.
Layton et al., "A clinical evaluation of acne scarring and its incidence", Clinical and Experimental Dermatology, 1994, 19:303-308.
Picardo et al., "Acne and Rosacea", Dermatological Therapy, 2017, 7:43-52.
Titus and Hodge, "Diagnosis and Treatment of Acne", American Family Physician, 2012, 86(8): 734-740.
Tuchayi et al., "Acne vulgaris", Nature Reviews Disease Primers, 2015,1:1-20.
Xu et al., "The analysis of acne increasing suicide risk", Medicine, 2021, 100(24):1-7.
Pappas, Apostolos et al., "Sebum analysis of individuals with and without acne", Dermato-Endocrinology, 2009, vol. 1:3, 157-161.

* cited by examiner

*Primary Examiner* — Timothy P Thomas
(74) *Attorney, Agent, or Firm* — Gorman IP Law, APC

(57) ABSTRACT

A topically administered synergistic composition for treating skin conditions, acne form lesions, and acne that simultaneously downregulates the production of TNF alpha, IL-1a, IL-8, Leptin, and Sebum in human skin as well as inhibiting bacterial biofilm growth on human skin as well as inhibition and/or prevention of inflammation in the pilosebaceous unit and/or hair follicle of human skin.

20 Claims, No Drawings

COMPOSITIONS AND METHODS FOR TREATING SKIN CONDITIONS, ACNE FORM LESIONS, AND ACNE

BACKGROUND

Acne is a disorder that affects the skin's oil glands and hair follicles known as the pilosebaceous unit (PSU). Plugged pores and outbreaks of lesions, commonly called pimples, occur on the face, neck, back, chest, and shoulders as well as less commonly other bodily surface areas. Herein we define "acne" as acne-form eruptions and includes: common acne vulgaris as well as other forms such as, but not limited to, acne cosmetic, papulopustular rosacea, halogen acne, occupational acne, tropical cane, and acne agminate.

Pilosebaceous units (PSUs) are found over most of the body. PSUs consist of a sebaceous gland connected to a canal, called a follicle, which contains a fine hair. The sebaceous glands have an acinar structure, in which multiple glands branch off a central duct. The primary cells of the sebaceous gland are sebocytes that produce an oily substance called sebum which the gland secretes. In healthy PSUs, the sebaceous glands make a limited amount of sebum that empties onto the skin surface through the opening of the follicle, called a pore. In abnormal states excess sebum is produced; examples of abnormal states are those when certain bacterial species are present in the gland and/or conditions that increase sebum production, such as the presence of excess amounts of hormones, for example androgen, leptin, and others.

The most common form of acne, known as acne vulgaris, is a long-term skin disease that occurs when dead skin cells and oil from the skin clog hair follicles.[10] Typical features of the condition include blackheads or whiteheads, pimples, oily skin, and possible scarring.[1][2][11] It primarily affects skin with a relatively high number of oil glands, including the face, upper part of the chest, and back.[12]. Oily skin is caused by an increased sebum secretion, and the subsequent interaction of sebum on the skin surface with sweat components results in a cosmetically undesired oily and shiny facial skin appearance, predominantly in the T-zone. (1,2). As noted above, there are several known factors causing increased sebum production including, androgenic steroid hormones.

Other forms of acne also exist; for example, acne associated with other co-existing medical conditions, such as diabetes, obesity, polycystic ovarian syndrome, and congenital adrenal hyperplasia. Regardless of cause the underlying pathophysiologic process in acne is inflammation of the PSU which is chronic and can ultimately lead to scarring and pigmentation changes in the skin of the affected area. The appearance of the skin that results from this can lead to anxiety, reduced self-esteem, and, in extreme cases, depression or thoughts of suicide.[3][4]

In addition to any predisposing underlying medical conditions, there are several more common predisposing factors to the occurrence of acne, especially acne vulgaris, including; diet, heredity, age, and skin microbiome.

Genetics is the primary predisposing factor in acne of all types. A study on acne in twins in the US showed that both twins had a high risk of inheriting acne. This was corroborated in an Australian study involving adolescent twins. When monozygotic versus dizygotic twins were studied for the composition and production of sebum, monozygotic twins showed a higher degree of correlation with regard to sebum excretion as well as the percentage of branched fatty acids in sebum from different individuals. Thus, previous studies showed a heritability estimate ranging from 50-90% for acne. In other words, approximately 50-90% of acne was due to genetic variation in the affected individuals. Another large UK study involving 400 twin pairs showed that 81% of acne was due to genetic factors. Inherited variants in human genes such as: LEP (leptin), TNF (tumor necrosis factor alpha), TLR2 (toll-like receptor 2), AR (androgen receptor), IGF-1 (insulin-like growth factor 1) and IL6 (interleukin 6) have all be associated with acne in human studies. Many of these genes are also associated with increased sebum production.

Dietary intake is clearly associated with predisposition to various forms of acne. For the most part, the Western diet predisposes to many forms of acne due to an induced inflammasomopathy of the sebaceous follicle and PSU (2). This diet is "rich" in red meat, saturated fats, dairy products, high carbohydrate, sweetened processed foods, and salt, with minimal intake of fruits, vegetables, fish, legumes, and whole grains.

In a sebum-rich skin environment, the naturally occurring and largely commensal skin bacterium *Cutibacrteium acnes* (also known as *C. acnes*) readily grows in sebum rich environments and can cause inflammation within and around the PSU. Thus, *C. acnes* triggers skin inflammation in acne by increasing the production of several pro-inflammatory chemical signals (such as IL-1$\alpha$, IL-8, TNF-$\alpha$) in human skin PSUs.

There exist many treatment modalities for acne; including laser-based therapies as well as various medications. However, none of the medical therapies have been shown to have simultaneous effect on the multiple pro-inflammatory, hyper-seborrhea, bacterial dysbiosis and innate immune defense pathways altered in acne. Thus, better agents that simultaneously reverse these pathogenic processes are needed. Unexpectedly, the inventor herein has discovered a specific combination of ingredients that simultaneously modulates multiple pathways involved in acne and reverses the disease process as well as preventing and/or mitigating further outbreaks, whereas the individual components of the composition do not demonstrate such an effect.

SUMMARY OF THE INVENTION

It has now been found that compositions comprising a *Garcinia* extract, a *Citrus* peel extract, Riboflavin, Beta-cyclodextrin, Manganese salts, and a polymer are effective when topically applied to prevent as well as treat acne-form lesions on human skin. The present invention then relates to topical compositions comprising *Garcinia* extract, *Citrus* peel extract, riboflavin, beta-cyclodextrin, manganese salts, and at least one polymer ingredient in a water base. The polymeric ingredient includes, but is not limited to, poly (meth)acrylate, hyaluronic acid, polylactic acid and co-polymers thereof, without any monohydric alcohols in the composition.

In one aspect, the composition comprises a *Garcinina* extract at 0.3-3.5 percent v/v, *Citrus* peel extract at 0.2-4.5 percent v/v, riboflavin at 0.01-0.05 percent w/v, beta-cyclodextrin at 0.8-4.6 percent w/v, manganese chloride at 0.015-0.60 percent w/v, and polymer at 0.1-7 percent w/v, with the remaining volume consisting of water at final pH of 4.7-8.4 at 25 degrees centigrade. In another aspect, the viscosity of the composition is 50-300 cps.

The present disclosure also relates to methods for simultaneously reducing pro-inflammatory cytokines in pilosebaceous units (PSUs) and/or hair follicles of the skin, decreasing sebum production in the PSUs, decreasing leptin production by cells in the PSU, while increasing naturally occurring anti-bacterial agents produced by the PSUs and reducing the presence of biofilms containing *C. acnes* bacterium in PSUs.

Various formulations for the cosmetic compositions are disclosed. Other features and advantages will become apparent from the following more detailed description.

DETAILED DESCRIPTION OF THE INVENTION

It has now been unexpectedly found that effective treatment and/or prevention of various acne-form skin lesions can be achieved with compositions comprising; *Garcinia* extract, *Citrus* peel extract, Riboflavin, Beta-cyclodextrin, Manganese salts, and at least one polymer ingredient in a water base. It has also been unexpectedly found that this combination of ingredients exhibits unexpected biological activities that none of the individual ingredients exhibit.

Definitions

As used in the description, and in the claims, the terms:

"Acne-form or acneiform lesion" as used herein refers to skin eruptions that resemble acne vulgaris. Lesions may be papulopustular, nodular, or cystic. Usually, but not always, they lack comedones clinically. Histopathologically, they are inflammations of the follicle or pilosebaceous unit.

"Acne" as used herein refers to conditions such as, but not limited to, acne vulgaris in which acneiform eruptions usually have comedones clinically. Most commonly they are inflammations of the pilosebaceous unit.

"Biological activity" as used herein means having an effect on or eliciting a response from a living cell, tissue, organ, or physiologic activity.

"Biomarker" as used herein means a measurable indicator of the severity or the presence of a particular disease state. More generally a biomarker is anything that can be used as an indicator of a particular disease state or some other physiological state of an organism.

"*C. acnes*" as used herein refers to the bacterium *Cutibacterium acnes*, formerly known as *Propionibacterium acnes*. The presence of this bacterium in follicles or pilosebaceous unit is known to be associated with acne and acneiform lesions.

"Monohydric alcohol" as used herein refers to an alcohol that has one hydroxyl group. Examples include, but are not limited to, methanol, ethanol, and isopropanol.

"Polymer" as used herein refers to a substance or material consisting of very large molecules, or macromolecules, composed of many repeating subunits. Polymers as used herein may be naturally occurring or may be synthetic.

The disclosed composition comprises a *Garcinia* extract, *Citrus* peel extract, riboflavin, beta-cyclodexrin, managanese chloride, and at least one polymer. The *Garcinia* extract is present at 0.1-4.0 percent v/v, 0.3-3.5 percent v/v, 0.3-3.0 percent v/v, 0.4-3.5 percent v/v, 0.5-3.5 percent v/v, 0.6-3.5 percent v/v, 0.8-3.5 percent v/v, 0.9-3.5 percent v/v, 1.0-3.5 percent v/v, 1.5-3.5 percent v/v, 2.0-3.5 percent v/v, 2.5-3.5 percent v/v, 3.0-3.5 percent v/v, 0.3-2.5 percent v/v, 0.3-2.0 percent v/v, 0.3-1.5 percent v/v, 0.3-1.0 percent v/v, 0.3-0.8 percent v/v, 0.3-0.5 percent v/v, 0.4-3.0 percent v/v, 0.5-3.0 percent v/v, 0.5-2.5 percent v/v, 0.5-2.0 percent v/v, 0.5-1.5 percent v/v, or 0.5-1.0 percent v/v, and all values in between those endpoints.

Suitable examples of *Garcinia* are, without limitation, *G. mangostana* (mangosteen), *G. indica* (kokum), *G. cambogia* (gamboge), *G. forbesii* (kandis), *G. prainiana* (button mangosteen), *G. multiflora*, *G. intermedia* (lemon drop mangosteen), *G. gummi-gutta* (kodumpulli), *G. kola* (bitter kola), *G. manii*, *G. subelliptica* (fukugi), and *G. hombroniana* (seashore mangosteen).

The *Citrus* peel extract is present at 0.1-5.0 percent v/v, 0.2-4.5 percent v/v, 0.2-4.5 percent v/v, 0.3-3.0 percent v/v, 0.4-4.5 percent v/v, 0.5-4.5 percent v/v, 0.6-4.5 percent v/v, 0.8-4.5 percent v/v, 0.9-4.5 percent v/v, 1.0-4.5 percent v/v, 1.5-4.5 percent v/v, 2.0-4.5 percent v/v, 2.5-4.5 percent v/v, 3.0-4.5 percent v/v, 3.5-4.5 percent v/v, 4.0-4.5 percent v/v, 0.2-4.0 percent v/v, 0.2-3.5 percent v/v, 0.2-3.0 percent v/v, 0.2-2.5 percent v/v, 02-2.0 percent v/v, 0.2-1.5 percent v/v, 0.2-1.0 percent v/v, 0.2-0.8 percent v/v, 0.2-0.5 percent v/v, 0.4-3.0 percent v/v, 0.5-3.0 percent v/v, 0.5-2.5 percent v/v, 0.5-2.0 percent v/v, 0.5-1.5 percent v/v, or 0.5-1.0 percent v/v, and all values in between those endpoints.

Suitable examples of *Citrus* are, without limitation, *C. unshui*, *C. reticulata* (mandarin), *C. japonica* (kumquat), *C. sinensis* (orange), *C. maxima* (pomelo), *C. medica* (citron), and *C. tangerina*.

Riboflavin is present at 0.009-0.1 percent w/v, 0.01-0.075 percent w/v, 0.01-0.05 percent w/v, 0.01-0.04 percent w/v, 0.01-0.03 percent w/v, 0.01-0.02 percent w/v, 0.02-0.0075 percent w/v, 0.02-0.05 percent w/v, 0.03-0.05 percent w/v, or 0.04-0.05 percent w/v, and all values in between those endpoints.

Beta-cyclodextrin is present at 1.0-4.8 percent w/v, 0.8-4.6 percent w/v, 0.8-4.5 percent w/v, 0.8-4.4 percent w/v, 0.8-4.3 percent w/v, 0.8-4.2 percent w/v, 0.8-4.1 percent w/v, 0.8-4.0 percent w/v, 0.8-3.9 percent w/v, 0.8-3.8 percent w/v, 0.8-3.7 percent w/v, 0.8-3.6 percent w/v, 0.8-3.5 percent w/v, 0.8-3.4 percent w/v, 0.8-3.3 percent w/v, 0.8-3.2 percent w/v, 0.8-3.1 percent w/v, 0.8-3.0 percent w/v, 0.8-2.9 percent w/v, 0.8-2.8 percent w/v, 0.8-2.7 percent w/v, 0.8-2.6 percent w/v, 0.8-2.5 percent w/v, 0.8-2.4 percent w/v, 0.8-2.3 percent w/v, 0.8-2.2 percent w/v, 0.8-2.1 percent w/v, 0.8-2.0 percent w/v, 0.8-1.9 percent w/v, 0.8-1.8 percent w/v, 0.8-1.7 percent w/v, 0.8-1.6 percent w/v, 0.8-1.5 percent w/v, 0.8-1.4 percent w/v, 0.8-1.3 percent w/v, 0.8-1.2 percent w/v, 0.8-1.1 percent w/v, 0.8-1.0 percent w/v, 0.8-0.9 percent w/v, 0.9-4.6 percent w/v, 1.0-4.6 percent w/v, 1.1-4.6 percent w/v, 1.2-4.6 percent w/v, 1.3-4.6 percent w/v, 1.4-4.6 percent w/v, 1.5-4.6 percent w/v, 1.6-4.6 percent w/v, 1.7-4.6 percent w/v, 1.8-4.6 percent w/v, 1.9-4.6 percent w/v, 2.0-4.6 percent w/v, 2.1-4.6 percent w/v, 2.2-4.6 percent w/v, 2.3-4.6 percent w/v, 2.4-4.6 percent w/v, 2.5-4.6 percent w/v, 2.6-4.6 percent w/v, 2.7-4.6 percent w/v, 2.8-4.6 percent w/v, 2.9-4.6 percent w/v, 3.0-4.6 percent w/v, 3.1-4.6 percent w/v, 3.2-4.6 percent w/v, 3.3-3.6 percent w/v, 3.4-4.6 percent w/v, 3.5-4.6 percent w/v, 3.6-4.6 percent w/v, 3.7-4.6 percent w/v, 3.8-4.6 percent w/v, 3.9-4.6 percent w/v, 4.0-4.6 percent w/v, 4.1-4.6 percent w/v, 4.2-4.6 percent w/v, 4.3-4.6 percent w/v, 4.4-4.6 percent w/v, or 4.5-4.6 percent w/v, and all values in between those endpoints.

Manganese chloride is present at 0.02-1.0 percent w/v, 0.0175-0.75 percent w/v, 0.015-0.60 percent w/v, 0.015-0.50 percent w/v, 0.015-0.40 percent w/v, 0.015-0.3 percent w/v, 0.015-0.2 percent w/v, 0.015-0.1 percent w/v, 0.015-0.05 percent w/v, 0.015-0.04 percent w/v, 0.015-0.03 percent w/v, 0.015-0.2 percent w/v, 0.02-0.60 percent w/v, 0.025-0.60 percent w/v, 0.03-0.60 percent w/v, 0.035-0.60 percent w/v, 0.04-0.60 percent w/v, 0.045-0.60 percent w/v, 0.05-0.60 percent w/v, 0.06-0.60 percent w/v, 0.0.07-0.60 percent w/v, 0.08-0.60 percent w/v, 0.09-0.60 percent w/v, 0.1-0.60 percent w/v, 0.2-0.60 percent w/v, 0.3-0.60 percent w/v, 0.4-0.60 percent w/v, or 0.5-0.60 percent w/v, and all values in between those endpoints.

Polymer is present at 0.1-10 percent w/v, 0.1-8 percent w/v, 0.1-7 percent w/v, 0.1-6 percent w/v, 0.1-6 percent w/v, 0.1-5 percent w/v, 0.1-4 percent w/v, 0.1-3 percent w/v, 0.1-2 percent w/v, 0.1-1 percent w/v, 0.1-0.75 percent w/v, 0.1-0.5 percent w/v, 0.2-7 percent w/v, 0.3-7 percent w/v, 0.4-7 percent w/v, 0.5-7 percent w/v, 0.6-7 percent w/v, 0.8-7 percent w/v, 0.9-7 percent w/v, 1-7 percent w/v, 2-7 percent w/v, 3-7 percent w/v, 4-7 percent w/v, 5-7 percent w/v, or 6-7 percent w/v, and all values in between those endpoints.

The remaining volume consists of water at a final pH of 4.5-8.6, 4.7-8.4, 4.8-8.4, 4.9-8.4, 5.0-8.4, 5.2-8.4, 5.4-8.4, 5.6-8.4, 5.8-8.4, 6.0-8.4, 6.2-8.4, 6.4-8.4, 6.6-8.4, 6.8-8.4, 7.0-8.4, 7.2-8.4, 7.4-8.4, 7.6-8.4, 7.8-8.4, 8.2-8.4, 4.7-8.2, 4.7-8.0, 4.7-7.8, 4.7-7.6, 4.7-7.4, 4.7-7.2, 4.7-7.0, 4.7-6.8, 4.7-6.6, 4.7-6.4, 4.7-6.2, 4.7-6.0, 4.7-5.8, 4.7-5.6, 4.7-5.4, 4.7-5.2, 4.7-5.0, or 4.7-4.9 and all values in between those endpoints at 25 degrees centigrade. In some cases, the viscosity of the composition is 45-350 cps, 50-300 cps, 75-300 cps, 100-300 cps, 150-300 cps, 200-300 cps, 250-300 cps, 45-300 cps, 50-250 cps, 50-200 cps, 50-150 cps, 50-100 cps, or 50-75 cps, and all values between those endpoints.

The composition disclosed can be prepared in the form of a solution, lotion, serum gel, cream, or ointment, and the like, suited to topical administration. The formulation of the compositions as solutions, gels, creams, lotions, serums, or ointments occurs by choice of appropriate carriers. Suitable carriers include deionized water, vegetable or mineral oils, and high molecular weight non-monohydric alcohols. Ideally, the carriers are those in which the active ingredients are soluble.

Emulsifiers, stabilizers, and antioxidants may also be included as well as agents imparting color or fragrance.

The efficacious ingredients, including the polymers, are best added to the formulation at temperatures below 50 degree centigrade.

The compositions disclosed herein unexpectedly provide highly effective treatments for acne-form lesions on the skin and reduce their recurrence without producing unwanted systemic or local side effects. The composition is applied topically. The composition can be in the form of a liquid, solution, lotion, serum, gel, cream, or ointment.

When the composition is a liquid, such as a solution, then it is usually necessary to dissolve the ingredients in water or another aqueous and non-aqueous pharmaceutically acceptable vehicle that does not include monohydric alcohols. The solution is then admixed, if desired, in a conventional manner with a suitable gel, cream, lotion, serum or ointment base in order to prepare the pharmaceutical composition in the form of a lotion, serum, gel, cream, or ointment.

Suitable carriers include deionized water, vegetable or mineral oils, branched chain fats or oils, animal fats, and/or high molecular weight non-monohydrate alcohol. The preferred carriers are those in which the active ingredients are soluble.

Emulsifiers, stabilizers, and antioxidants may also be included as well as agents imparting color or fragrance.

The composition disclosed exhibits synergistic behavior, showing improved efficacy over each of the individual components when analyzed for inflammatory mediators that are associated with acne and folliculitis, such as interleukin 6 (IL-6) and interleukin 8 (IL-8). Similarly, while each of the individual components of the composition had no effect on altering the abnormal ratio of polyunsaturated fatty acids (PUFA) to saturated fatty acids (SFA) in an acne-type sebocyte model system, treatment of those cells with the composition returned the ratio of polyunsaturated fatty acids (PUFA) to saturated fatty acids (SFA) to normal values.

Synergistic behavior of the composition was also seen in keratinocytes, where increased production of some biomarkers is associated with exposure to cultivated *C. acnes* or heat killed *C. acne*. Again, individual components had no effect on pretreatment of keratinocytes, while pretreatment with the composition inhibited production of IL-8, protease activated receptor 2 (PAR2), and involucrin (IVL) biomarkers.

Likewise, while none of the individual components inhibited *C. acnes* growth in vitro when added to cultivation media in amounts proportional to their concentration in the composition, addition of 1% of the composition to the media resulted in the inhibition of *C. acnes* growth.

EXAMPLES

In Vitro

In vitro human sebocyte and keratinocyte cells and tissues were cultivated under standard conditions. The cultivated human sebocytes and keratinocytes were then challenged with various stimuli associated with acne-form lesions and acne, such as IGF-1, heat killed *Cutibacterium acnes* cells, and bacterial products such as lipoteichoic acid. These stimuli are known to increase sebum production, increase pro-inflammatory cytokine production and alter biomarkers for cellular differentiation. These biomarkers are also increased in human acne and acne-form lesions. Cells were then treated with the ingredients of the composition individually and in combination. After treatment, the levels of expression genes, proteins and lipids in stimulated cells and tissues known to be altered in acne and acne-form lesions (i.e. biomarkers) were determined and compared for increases or decreases induced by treatment with the ingredients of composition, individually and in combination(s). A bioactivity profile of each individual ingredient was then created as well as a bioactivity profile of all the ingredients combined into a single mixture in proportion to the disclosed compositions.

1) Human Sebocytes Cultures

Sebaceous glands and sebocytes are capable of responding to different stimuli by altering production and secretion of lipids as well as production of inflammatory mediators that are associated with acne and folliculitis.

Human sebocytes were treated with Insulin like growth factor 1 (IGF-1) at 20 nM concentration; this induced up regulation for both interleukin 6 (IL-6) and interleukin 8 (IL-8). Pre-treatment of these cells with each individual component of the disclosed composition revealed that Mangosteen extract reduced production of IL-6 alone whereas none of the other individual components had an effect on IL-6 production. Surprisingly, however, the mixture of all components reduced the production of both IL-6 and IL-8; IL-6 was reduced 5-fold more with the mixture than with Mangosteen alone.

Next, the production of lipids by IGF-1 treated sebocytes was measured in comparison to sebocytes not treated with IGF-1. Here, the treated sebocytes demonstrated a different lipid production profile. IGF-1 induced an increase in triglycerides. Similarly, the ratio of polyunsaturated fatty acids (PUFA) to saturated fatty acids (SFA) was different in IGF-1 treated cells. The IGF treated cells demonstrated a marked increase in the presence of PUFA. Pre-treatment of these cells by the individual components of the disclosed composition did not have an effect on the IGF-1 induced differences in lipogenesis in the sebocytes. However, the mixture had the effect of reverting the PUFA/SFA ratio to the normal ratio found in cells not treated with IGF-1. Analysis of gene expression in the cells did not demonstrate any significant difference in gene expression, thus we conclude that the effect is mediated by metabolic changes induced in sebocytes treated by our composition.

2) Human Keratinocyte Cultures

Keratinocytes found in hair follicles and pilosebaceous units are capable of responding to stimuli such as the presence of *C. acnes* bacterial cells as well as the products of their metabolism such as lipoteichoic acid). The stimuli response is to produce cytokines and other pro-inflammatory biomarkers such as: interleukin 1 alpha (IL-1a), interleukin 8 (IL-8), tumor necrosis factor alpha (TNF-a) and insulin-like growth factor 1 (IGF-1), protease activated receptor 2 (PAR2) as well biomarkers of keratinocyte differentiation such as involucrin (IVL), filaggrin (FLG), and keratin (K17).

Cultivated human keratinocytes were stimulated using the media supernatant of cultivated *C. acnes* or heat killed *C. acne*. The treatment increased the production of IL-8, PAR-2, and IVL. Pre-treatment of the keratinocytes with each individual component of the composition did not inhibit the increased production of the biomarkers induced by the *C. acnes* cells or *C. acnes* culture supernatant. However, pre-treatment using the combination of the individual ingredients inhibited the increased production of the biomarkers induced by the *C. acnes* cells or *C. acnes* culture supernatant 3) *C. acnes* Culture To determine if the composition inhibited growth of *C. acnes* in culture a strain of the bacterium (ATCC® 11827™) was cultivated in growth media supplied by manufacturer (American Type Culture Collection, Manassas, Va.). The result of cultivation in the media along with 1% of the composition resulted in the inhibition of *C. acnes* growth. However, none of the individual components when added to the media in amounts proportional to their concentration in the composition inhibited *C. acnes* growth.

In sum, our results demonstrated that several but not all of the ingredients when tested alone modulated some but not all biomarkers. Several of the ingredients when tested alone had no effect of the biomarkers. However, unexpectedly, when all ingredient were combined all of the biomarkers were modulated in the in the opposite direction of the bio-marker pattern produced by the stimulants. Moreover, only the combination of the components was effective in inhibiting *C. acnes* growth. This indicates an unexpected synergistic effect of the components when combined together according to our composition.

I claim:

1. A method of treating acne in a subject comprising the topical administration to a patient in need thereof an effective amount of a composition comprising:
    (a) *Garcinia* extract selected from the group consisting of *G. mangostana, G. indica, G. cambogia, G. forbesii, G. prainiana, G. multiflora, G. intermedia, G. gummi-gutta, G. kola, G. manii, G. subelliptica*, and *G. hombroniana*, wherein the *Garcinia* extract is 0.3-3.5 percent v/v;
    (b) *Citrus* peel extract selected from the group consisting of *C. unshi, C. tangerina, C. japonica, C. sinensis, C. maxima, C. medica*, and *C. reticulata*, wherein the *Citrus* extract is 0.2-4.5 percent v/v;
    (c) Riboflavin, wherein the riboflavin is 0.01-0.05 percent w/v;
    (d) Beta-cyclodextrin, wherein the beta-cyclodextrin is 0.8-4.6 percent w/v;
    (e) Manganese chloride, wherein the manganese chloride is 0.015-0.6 percent w/v; and
    (f) at least one polymer selected from the group consisting of poly(meth)acrylate, hyaluronic acid, polylactic acid, and copolymers thereof, wherein the polymer is 0.1-7 percent w/v,
wherein the composition is administered in a water based topical formulation not containing any monohydric alcohol.

2. A method of simultaneously downregulating the production of TNF alpha, IL-1a, IL-6, IL-8, Leptin, and Sebum in human skin and inhibiting bacterial biofilm growth on human skin by administrating to a patient in need thereof an effective amount of a composition comprising
    (a) *Garcinia* extract selected from the group consisting of *G. mangostana, G. indica, G. cambogia, G. forbesii, G. prainiana, G. multiflora, G. intermedia, G. gummi-gutta, G. kola, G. manii, G. subelliptica*, and *G. hombroniana*, wherein the *Garcinia* extract is 0.3-3.5 percent v/v;
    (b) *Citrus* peel extract selected from the group consisting of *C. unshi, C. tangerina, C. japonica, C. sinensis, C. maxima, C. medica*, and *C. reticulata*, wherein the *Citrus* extract is 0.2-4.5 percent v/v;
    (c) Riboflavin, wherein the riboflavin is 0.01-0.05 percent w/v;
    (d) Beta-cyclodextrin, wherein the beta-cyclodextrin is 0.8-4.6 percent w/v;
    (e) Manganese chloride e. wherein the manganese chloride is 0.015-0.6 percent w/v; and
    (f) at least one polymer selected from the group consisting of poly(meth)acrylate, hyaluronic acid, polylactic acid, and copolymers thereof, wherein the polymer is 0.1-7 percent w/v,
wherein the composition is administered in a water based topical formulation not containing any monohydric alcohol.

3. The method according to claim 2, wherein the *Garcinia* extract is selected from the group consisting of *G. mangostana, G. prainiana, G. multiflora, G. intermedia, G. gummi-gutta*, and *G. hombroniana*.

4. The method according to claim 2, wherein the *Citrus* extract is selected from the group consisting of *C. unshui, C. maxima*, and *C. medica*.

5. The method according to claim 2, wherein the polymer is selected from the group consisting of poly(meth)acrylate, hyaluronic acid, and polylactic acid.

6. The method according to claim 2, wherein the *Garcinia* extract is *G. mangostana* extract, the *Citrus* extract is *C. unshui*, and the polymer is poly(meth)acrylate.

7. The method according to claim 1, wherein the *Garcinia* extract is *G. mangostana* extract, the *Citrus* extract is *C. unshui*, and the polymer is poly(meth)acrylate.

8. The method according to claim 2, wherein the simultaneous downregulation occurs in the pilosebaceous units of the skin.

9. The method according to claim 1, wherein the simultaneous downregulation occurs in the pilosebaceous units of the skin.

10. The method according to claim 6, wherein the simultaneous downregulation occurs in the pilosebaceous units of the skin.

11. The method according to claim 2, wherein the
(a) *Garcinia* extract is 1 percent v/v;
(b) *Citrus* peel extract is 3 percent v/v;
(c) Riboflavin is 0.05 percent w/v;
(d) Beta-cyclodextrin is 4 percent w/v;
(e) Manganese chloride is 0.3 percent w/v; and
(f) at least one polymer is 2 percent w/v.

12. The method according to claim 1, wherein the
(a) *Garcinia* extract is 1 percent v/v;
(b) *Citrus* peel extract is 3 percent v/v;
(c) Riboflavin is 0.05 percent w/v;
(d) Beta-cyclodextrin is 4 percent w/v;
(e) Manganese chloride is 0.3 percent w/v; and
(f) at least one polymer is 2 percent w/v.

13. The method according to claim 6, wherein the
(a) *Garcinia* extract is 1 percent v/v;
(b) *Citrus* peel extract is 3 percent v/v;
(c) Riboflavin is 0.05 percent w/v;
(d) Beta-cyclodextrin is 4 percent w/v;
(e) Manganese chloride is 0.3 percent w/v; and
(f) at least one polymer is 2 percent w/v.

14. The method according to claim 7, wherein the
(a) *Garcinia* extract is 1 percent v/v;
(b) *Citrus* peel extract is 3 percent v/v;
(c) Riboflavin is 0.05 percent w/v;
(d) Beta-cyclodextrin is 4 percent w/v;
(e) Manganese chloride is 0.3 percent w/v; and
(f) at least one polymer is 2 percent w/v.

15. The method according to claim 2, wherein the composition further comprises a carrier, an emulsifier, a stabilizer, an antioxidant, a color, and/or a fragrance.

16. The method according to claim 1, wherein the composition further comprises a carrier, an emulsifier, a stabilizer, an antioxidant, a color, and/or a fragrance.

17. The method according to claim 6, wherein the composition further comprises a carrier, an emulsifier, a stabilizer, an antioxidant, a color, and/or a fragrance.

18. The method according to claim 7, wherein the composition further comprises a carrier, an emulsifier, a stabilizer, an antioxidant, a color, and/or a fragrance.

19. The method according to claim 2, wherein the patient has acne or is infected with *Cutibacterium acnes*.

20. The method according to claim 6, wherein the patient has acne or is infected with *Cutibacterium acnes*.

\* \* \* \* \*